(12) United States Patent
Takeshima

(10) Patent No.: US 8,885,919 B2
(45) Date of Patent: Nov. 11, 2014

(54) SEMICONDUCTOR FAULT ANALYSIS DEVICE AND FAULT ANALYSIS METHOD

(75) Inventor: Tomochika Takeshima, Hamamatsu (JP)

(73) Assignee: Hamamatsu Photonics K.K., Hamamatsu-shi, Shizuoka (JP)

( * ) Notice: Subject to any disclaimer, the term of this patent is extended or adjusted under 35 U.S.C. 154(b) by 118 days.

(21) Appl. No.: 13/643,415

(22) PCT Filed: Feb. 21, 2011

(86) PCT No.: PCT/JP2011/053728
§ 371 (c)(1), (2), (4) Date: Oct. 25, 2012

(87) PCT Pub. No.: WO2011/135902
PCT Pub. Date: Nov. 3, 2011

(65) Prior Publication Data
US 2013/0039565 A1    Feb. 14, 2013

(30) Foreign Application Priority Data

Apr. 28, 2010   (JP) ................. 2010-103876

(51) Int. Cl.
| | |
|---|---|
| *G06K 9/00* | (2006.01) |
| *G06T 7/20* | (2006.01) |
| *G01N 25/72* | (2006.01) |
| *G06T 7/00* | (2006.01) |
| *G01R 31/311* | (2006.01) |

(52) U.S. Cl.
CPC .............. *G01N 25/72* (2013.01); *G06T 7/2033* (2013.01); *G06T 2207/20021* (2013.01); *G06T 2207/10048* (2013.01); *G06T 2207/30148* (2013.01); *G06T 7/0004* (2013.01); *G06T 2207/20224* (2013.01); *G06T 2207/10016* (2013.01); *G01R 31/311* (2013.01); *G06T 2207/20076* (2013.01)
USPC ........................... 382/145; 382/149; 382/151

(58) Field of Classification Search
USPC .......................... 382/144, 145, 147, 149, 151
See application file for complete search history.

(56) References Cited

U.S. PATENT DOCUMENTS 6,002,792 A * 12/1999 Oguri et al. .................... 382/145
7,474,115 B1 * 1/2009 Trujillo et al. ............ 324/762.07
(Continued)

FOREIGN PATENT DOCUMENTS

| | | |
|---|---|---|
| JP | 6-281700 | 10/1994 |
| JP | 7-311168 | 11/1995 |
| JP | 9-266238 | 10/1997 |
| JP | 2758562 | 5/1998 |

(Continued)

*Primary Examiner* — John Strege
(74) *Attorney, Agent, or Firm* — Drinker Biddle & Reath LLP

(57) ABSTRACT

A failure analysis apparatus 1A is provided with a voltage applying unit 14 for applying a bias voltage to a semiconductor device S, an imaging device 18 for acquiring an image, and an image processing unit 30 for performing image processing, and the imaging device 18 acquires a plurality of analysis images each including a thermal image in a voltage applied state and a plurality of background images in a voltage non-applied state. The image processing unit 30 includes an imaging position calculating section 32 for calculating an imaging position of each of the analysis images and the background images, an image classifying section 33 for classifying the analysis images and the background images into N image groups based on a region division unit prepared for the imaging position, and a difference image generating section 34 for generating difference images between the analysis images and the background images individually for N image groups. Accordingly, a semiconductor failure analysis apparatus and method capable of suppressing the effect of a shift in imaging position in a thermal analysis image of a semiconductor device can be realized.

16 Claims, 12 Drawing Sheets

(56) References Cited

U.S. PATENT DOCUMENTS

| | | |
|---|---|---|
| 7,805,691 B2 * | 9/2010 | Majima et al. ............... 716/112 |
| 7,865,012 B2 * | 1/2011 | Majima et al. ............... 382/149 |
| 2009/0238444 A1 * | 9/2009 | Su et al. ....................... 382/149 |
| 2014/0002125 A1 * | 1/2014 | Nakanishi et al. ....... 324/761.01 |

FOREIGN PATENT DOCUMENTS

| | | |
|---|---|---|
| JP | 11-337511 | 12/1999 |
| JP | 2003-303746 | 10/2003 |
| JP | 2007-24669 | 2/2007 |
| JP | 2009-288090 | 12/2009 |

* cited by examiner (a)

(b)

(a)

(b)

(a)

(b)

(a)

(b)

(a)

(b)

SEMICONDUCTOR FAULT ANALYSIS DEVICE AND FAULT ANALYSIS METHOD

TECHNICAL FIELD

The present invention relates to a semiconductor failure analysis apparatus for performing a failure analysis by means of a thermal image of a semiconductor device and a semiconductor failure analysis method.

BACKGROUND ART

Conventionally, as apparatuses for performing failure analyses of semiconductor devices, failure analysis apparatuses that detect heat generated in the semiconductor devices to locate failures thereof have been used. In such a failure analysis apparatus, for example, a bias voltage is applied to an electronic circuit included in the semiconductor device. Then, a thermal image is acquired by imaging the semiconductor device by means of an imaging device having sensitivity in a wavelength range of infrared light, and by analyzing the thermal image, heat generation in the semiconductor device is located (refer to, for example, Patent Documents 1 to 3).

CITATION LIST

Patent Literature

Patent Document 1: Japanese Patent Publication No. 2758562
Patent Document 2: Japanese Patent Application Laid-Open No. H9-266238
Patent Document 3: Japanese Patent Application Laid-Open No. H11-337511

SUMMARY OF INVENTION

Technical Problem

In the semiconductor failure analysis apparatus described above, a semiconductor device image to be acquired by the infrared imaging device includes a thermal image due to heat generated in the semiconductor device and a pattern image due to a circuit pattern in the semiconductor device. In this case, as a method for removing the pattern image and extracting the thermal image from such an image, a difference method is considered. That is, separately from an analysis image consisting of a thermal image plus a pattern image in a state where a bias voltage is applied to a semiconductor device, a background image consisting only of a pattern image in a state where a bias voltage is not applied thereto is acquired. Then, by taking a difference between the analysis image and the background image, only the thermal image can be extracted.

Here, in the above-described method, normally, the analysis image and background image are acquired in plural numbers in time series, respectively, and used for a failure analysis. On the other hand, in such a failure analysis apparatus, temperature drift occurs in which the imaging position with respect to the semiconductor device by the imaging device varies under the influence of changes in temperature. That is, when the temperature changes while acquiring analysis images and background images in time series, positional variation occurs as a result of the components of the failure analysis apparatus expanding and contracting on different conditions according to their difference in material and size and the like, and thus the imaging position shifts.

Such a shift in imaging position due to temperature cannot be completely eliminated because the apparatus itself is the source of heat generation and there are also causes such as inflow and outflow of outside air involved in loading and unloading of samples. Further, if a difference image corresponding to a thermal image is generated for analysis images and background images acquired with a shift in imaging position occurred, an edge portion of the circuit pattern in the semiconductor device appears as noise in the difference image (an edge noise component). Such an edge noise component poses a problem in performing a failure analysis of the semiconductor device by means of the thermal image.

The present invention has been made in order to solve the above problem, and an object thereof is to provide a semiconductor failure analysis apparatus, failure analysis method, and failure analysis program capable of suppressing the effect of a shift in imaging position in a thermal analysis image of a semiconductor device.

Solution to Problem

In order to achieve such an object, a semiconductor failure analysis apparatus according to the present invention is a semiconductor failure analysis apparatus for performing a failure analysis by means of a thermal image of a semiconductor device, including (1) voltage applying means applying a bias voltage to a semiconductor device to serve as an analysis object, (2) imaging means acquiring an image of the semiconductor device, and (3) image processing means performing image processing necessary for a failure analysis of the semiconductor device for an image acquired by the imaging means, in which (4) the imaging means acquires a plurality of analysis images each including a thermal image in a state where the bias voltage is applied to the semiconductor device and a plurality of background images in a state where the bias voltage is not applied thereto, and (5) the image processing means includes imaging position calculating means calculating, for each of the plurality of analysis images and the plurality of background images, an imaging position thereof, image classifying means preparing, for the imaging position of each of the plurality of analysis images and the plurality of background images, a region division unit set with reference to a position frequency distribution of the imaging positions, and classifying the plurality of analysis images and the plurality of background images into N image groups (N is an integer not less than 2) according to which of the N regions divided in accordance with the region division unit the imaging position belongs to, and difference image generating means generating a difference image between the analysis image and the background image to be used for a failure analysis, individually for the classified N image groups.

Moreover, a semiconductor failure analysis method according to the present invention is a semiconductor failure analysis method for performing a failure analysis by means of a thermal image of a semiconductor device, including (1) a voltage applying step of applying a bias voltage to a semiconductor device to serve as an analysis object, (2) an imaging step of acquiring an image of the semiconductor device, and (3) an image processing step of performing image processing necessary for a failure analysis of the semiconductor device for an image acquired by the imaging step, in which (4) the imaging step acquires a plurality of analysis images each including a thermal image in a state where the bias voltage is applied to the semiconductor device and a plurality of background images in a state where the bias voltage is not applied thereto, and (5) the image processing step includes an imaging position calculating step of calculating, for each of the plurality of analysis images and the plurality of background images, an imaging position thereof, an image classifying step of preparing, for the imaging position of each of the plurality of analysis images and the plurality of background images, a region division unit set with reference to a position frequency distribution of the imaging positions, and classifying the plurality of analysis images and the plurality of background images into N image groups (N is an integer not less than 2) according to which of the N regions divided in accordance with the region division unit the imaging position belongs to, and a difference image generating step of generating a difference image between the analysis image and the background image to be used for a failure analysis, individually for the classified N image groups.

Moreover, a semiconductor failure analysis program according to the present invention is a program to be applied to a semiconductor failure analysis apparatus which includes (a) voltage applying means applying a bias voltage to a semiconductor device to serve as an analysis object, and imaging means acquiring an image of the semiconductor device, and performs a failure analysis by means of a thermal image of the semiconductor device, and in which (b) the imaging means acquires a plurality of analysis images each including a thermal image in a state where the bias voltage is applied to the semiconductor device and a plurality of background images in a state where the bias voltage is not applied thereto, and (c) for causing a computer to execute image processing necessary for a failure analysis of the semiconductor device for an image acquired by the imaging means, and causes the computer to execute (d) an imaging position calculating process of calculating, for each of the plurality of analysis images and the plurality of background images, an imaging position thereof, (e) an image classifying process of preparing, for the imaging position of each of the plurality of analysis images and the plurality of background images, a region division unit set with reference to a position frequency distribution of the imaging positions, and classifying the plurality of analysis images and the plurality of background images into N image groups (N is an integer not less than 2) according to which of the N regions divided in accordance with the region division unit the imaging position belongs to, and (f) a difference image generating process of generating a difference image between the analysis image and the background image to be used for a failure analysis, individually for the classified N image groups.

In the semiconductor failure analysis apparatus, method, and program described above, an analysis image of a thermal image plus a pattern image in a state where a bias voltage is applied to the semiconductor device and a background image of only a pattern image in a state where a bias voltage is not applied are acquired in time series in plural numbers, respectively. Then, an imaging position is calculated for each of the analysis images and background images, and a region division unit is prepared for variation in imaging position, the analysis images and background images are classified into N image groups by means of the N regions divided by the region division unit, and generation of difference images for which thermal images are extracted is performed.

In the above-described configuration, the plurality of analysis images and the plurality of background images are classified into the N image groups according to the position shift amount of a shift in imaging position, and difference images are generated for each of the image groups after classification. According to such a configuration, by appropriately setting a region division unit, the effect of a shift in imaging position can be reduced to suppress generation of noise such as an edge noise component due to a shift in imaging position in a difference image to be used for a failure analysis of the semiconductor device.

In terms of generation of difference images between analysis images and background images to be performed for the N image groups for each of the image groups, there may be a configuration for generating a difference image for each of the N image groups, according to a specific method etc., for a failure analysis of the semiconductor device, and acquiring N difference images. Alternatively, there may be a configuration for generating a difference image for at least one of the N image groups.

Advantageous Effects of Invention

According to the semiconductor failure analysis apparatus, method, and program of the present invention, acquiring an analysis image in a state where a bias voltage is applied to a semiconductor device of an analysis object and a background image in a state where a bias voltage is not applied in plural numbers, calculating an imaging position for each of the analysis images and background images, and preparing a region division unit for variation in imaging position, classifying the analysis images and background images into N image groups by means of the N regions divided by the region division unit, and performing generation of difference images corresponding to thermal images allows suppressing the effect of a shift in imaging position in a thermal analysis image of the semiconductor device.

DESCRIPTION OF EMBODIMENTS

Figure 1:
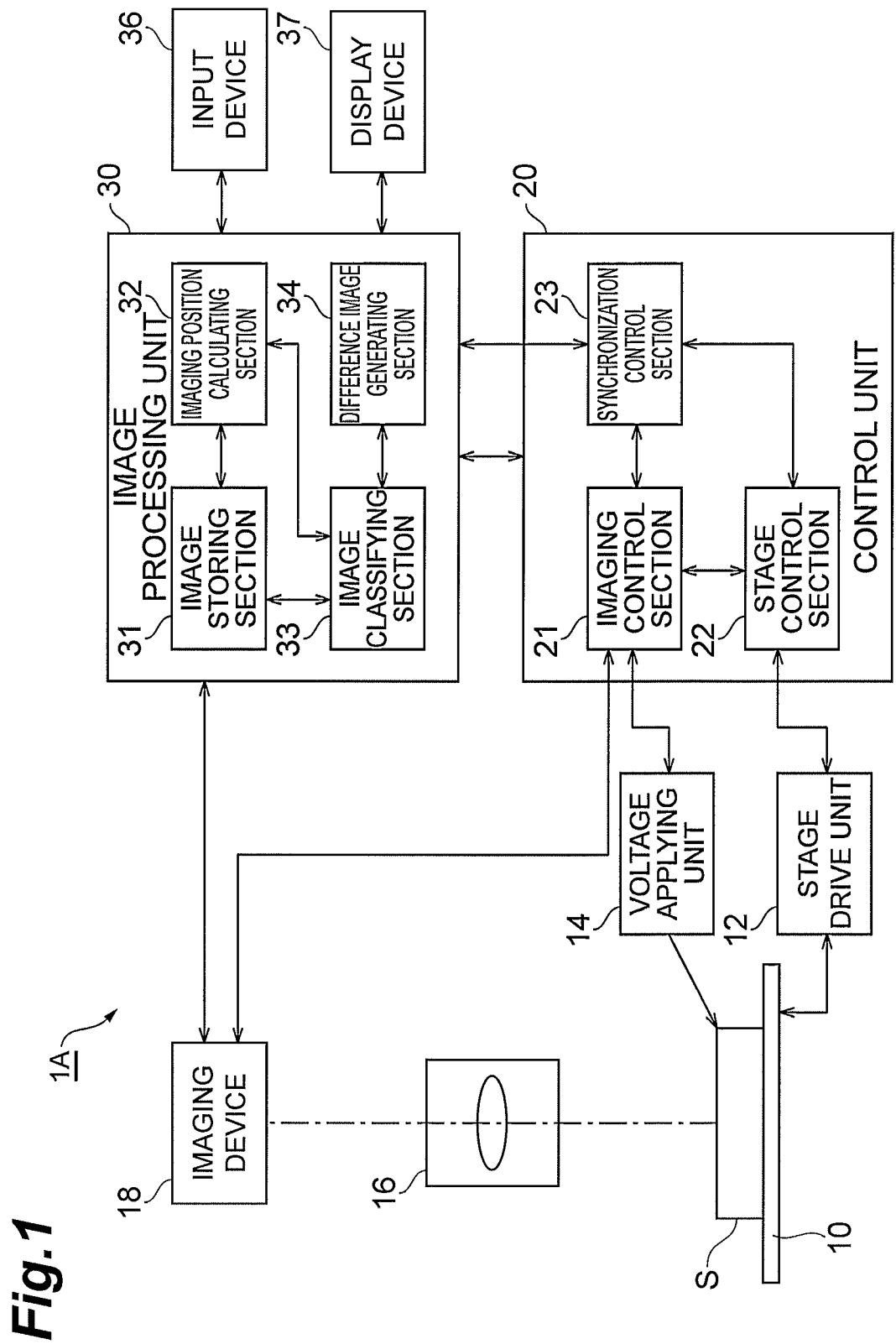
FIG. 1 is a block diagram showing the configuration of an embodiment of a semiconductor failure analysis apparatus.

Hereinafter, preferred embodiments of a semiconductor failure analysis apparatus, failure analysis method, and failure analysis program according to the present invention will be described in detail along with the drawings. In the description of the drawings, the same components are denoted by the same reference symbols, and overlapping description will be omitted. The dimensional ratios in the drawings are not always the same as those in the description.

FIG. 1 is a block diagram schematically showing the configuration of an embodiment of a semiconductor failure analysis apparatus according to the present invention. The apparatus 1A is a failure analysis apparatus for performing a failure analysis by means of a thermal image of a semiconductor device S. The semiconductor failure analysis apparatus 1A shown in FIG. 1 is provided with a sample stage 10, a voltage applying unit 14, an imaging device 18, a control unit 20, and an image processing unit 30.

The semiconductor device S to serve as an analysis object is placed on the sample stage 10 using an XYZ stage that can be driven in the X-axis direction, Y-axis direction (horizontal direction), and Z-axis direction (vertical direction), respectively. The stage 10 is arranged so as to be driven in the X-, Y-, and Z-directions by a stage drive unit 12, and thereby, imaging focusing onto the semiconductor device S, alignment in imaging position, and the like are performed. Above the stage 10, an imaging device 18 that is imaging means for acquiring a two-dimensional image of the semiconductor device S is located. As the imaging device 18, an imaging device having sensitivity in a predetermined wavelength range, for example, an infrared imaging device having sensitivity in an infrared light wavelength range, is suitably used in order to acquire an image by a thermal image of the semiconductor device S.

On the optical axis between the stage 10 and the imaging device 18, a light guide optical system 16 for guiding an image of the semiconductor device 10 to the imaging device 18 is provided. Moreover, for the semiconductor device S on the stage 10, a voltage applying unit 14 is provided. The voltage applying unit 14 is voltage applying means for applying a necessary bias voltage to an electronic circuit of the semiconductor device S when performing a failure analysis by a thermal image, and contains a power supply for voltage application. In terms also of the light guide optical system 16, a drive mechanism such as an XYZ stage is provided, if necessary.

In such a configuration, the imaging device 18 acquires an analysis image in a state where a bias voltage is applied to the semiconductor device S by the voltage applying unit 14 and a background image in a state where a bias voltage is not applied thereto are acquired in time series in plural numbers, respectively. The analysis image to be acquired in a voltage applied state is an image including a thermal image of the semiconductor device S and a pattern image due to a circuit pattern in the semiconductor device S. On the other hand, the background image to be acquired in a voltage non-applied state is an image including only a pattern image of the semiconductor device S.

In the failure analysis apparatus 1A shown in FIG. 1, for the stage 10, the stage drive unit 12, the voltage applying unit 14, the light guide optical system 16, and the imaging device 18, a control unit 20 for controlling the operation thereof is provided. The control unit 20 in the present embodiment is configured having an imaging control section 21, a stage control section 22, and a synchronization control section 23.

The imaging control section 21 controls acquisition of analysis images and background images of the semiconductor device S by controlling a bias voltage application operation by the voltage applying unit 14 and an image acquisition operation by the imaging device 18. The stage control section 22 controls the operation (moving operation of the semiconductor device S on the stage 10) of the XYZ stage 10 and the stage drive unit 12. The synchronization control section 23 performs control for gaining synchronization necessary between the imaging control section 21 and the stage control section 22, and the image processing unit 30 provided for the imaging device 18.

The image processing unit 30 is image processing means for performing image processing necessary for a failure analysis of the semiconductor device S for an image acquired by the imaging device 18. The image processing unit 30 in the present embodiment is configured having an image storing section 31, an imaging position calculating section 32, an image classifying section 33, and a difference image generating section 34. An image of the semiconductor device S acquired by the imaging device 18 is input to the image processing unit 30, and stored and accumulated in the image storing section 31 according to necessity.

The imaging position calculating section 32 calculates, for each of the plurality of analysis images and the plurality of background images of the semiconductor device S acquired by the imaging device 18, an imaging position within a horizontal plane (within an X-Y plane) thereof. Here, in image acquisition in the failure analysis apparatus 1A, the imaging position with respect to the semiconductor device S varies under the influence of changes in temperature (temperature drift). Moreover, the imaging position also varies due to vibration etc., in the apparatus 1A. The imaging position calculating section 32 determines the thus varying imaging position for each image, and evaluates a position shift amount thereof. Here, the level of such variation in imaging position is, normally, a level smaller than the pixel size of the imaging device 18.

The image classifying section 33 prepares, for the imaging position of each of the plurality of analysis images and the plurality of background images, a region division unit set with reference to a position frequency distribution thereof. Then, the image classifying section divides the distribution of the imaging positions into N regions (N is an integer not less than 2) in accordance with the region division unit, and classifies the analysis images and background images into N image groups according to which of the N divided regions the imaging position belongs to. Here, when the variation in imaging position is smaller than the pixel size as in the above, the region division unit to be used for image classification is set smaller than the pixel size, and image grouping is performed with a positional accuracy smaller than the pixel size.

The difference image generating section 34 generates difference images between the analysis images and background images to be used for a failure analysis, individually for the N image groups classified by the image classifying section 33. Here, the analysis image is an image including a thermal image and a pattern image as described above, while the background image is an image including only a pattern image. Therefore, a difference image being a difference taken therebetween results in an image for which only the thermal image necessary for a failure analysis is extracted. Then, by locating heat generation in the difference image, a failure analysis of the semiconductor device is performed.

Such an image processing unit 30 is configured using, for example, a computer. Moreover, to the image processing unit 30, an input device 36 and a display device 37 are connected. The input device 36 is configured by, for example, a keyboard, a mouse, and the like, and used for input etc., of information and instructions necessary for executing an image acquisition operation and a failure analysis operation in the present apparatus 1A. Moreover, the display device 37 is configured by, for example, a CRT display, a liquid crystal display, or the like, and used for display etc., of necessary information concerning image acquisition and a failure analysis in the present apparatus 1A.

Here, in terms of the image processing unit 30, there may be a configuration for being embodied together with the control unit 20 by a single control device (for example, a single computer). Moreover, in terms also of the input device 36 and the display device 37 to be connected to the image processing unit 30, similarly, there may be a configuration for functioning as input and display devices not only for the image processing unit 30 but also for the control unit 20.

Figure 2:
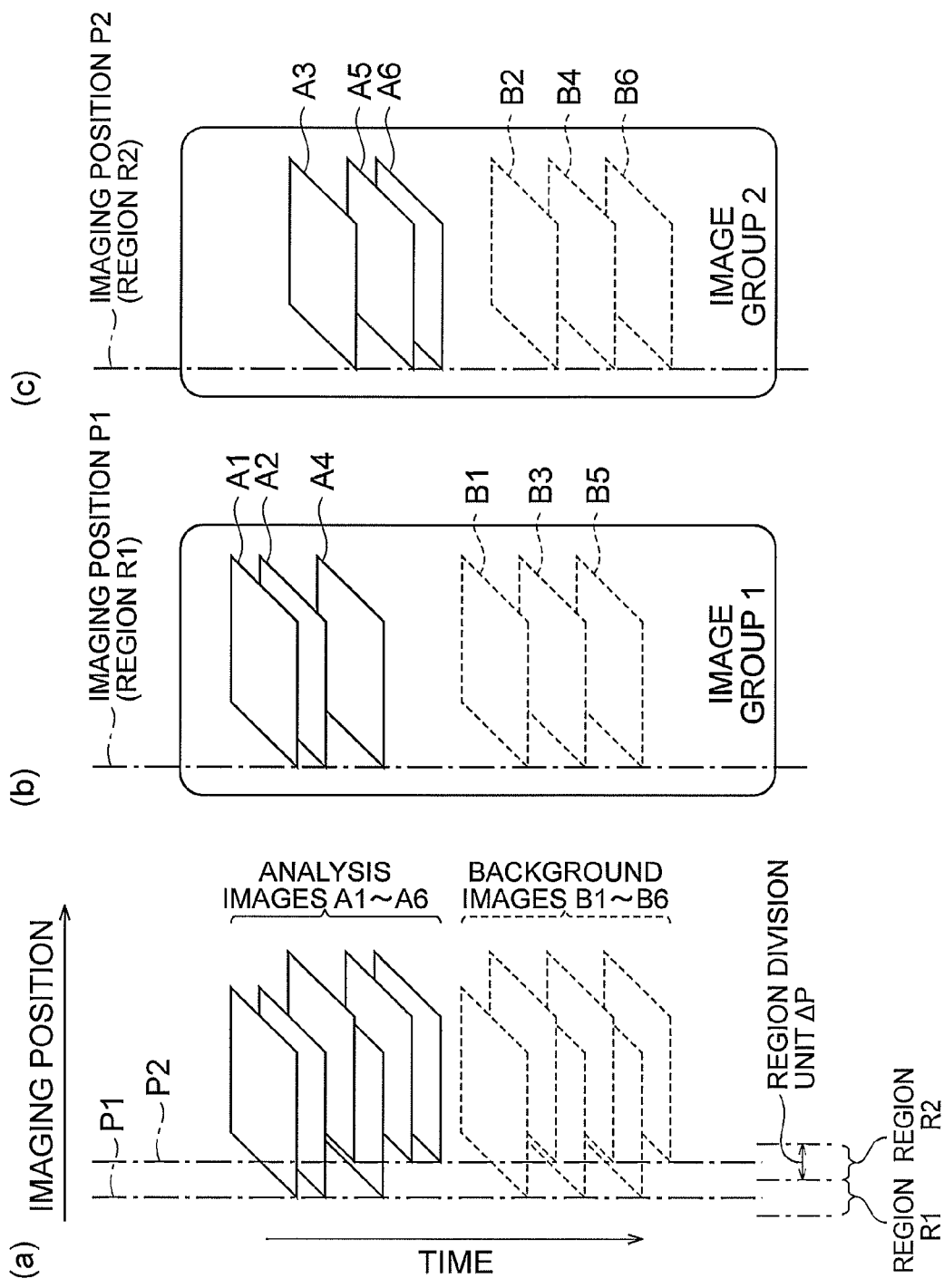
FIG. 2 includes views schematically showing a failure analysis method to be executed in the semiconductor failure analysis apparatus shown in FIG. 1.
Figure 3:
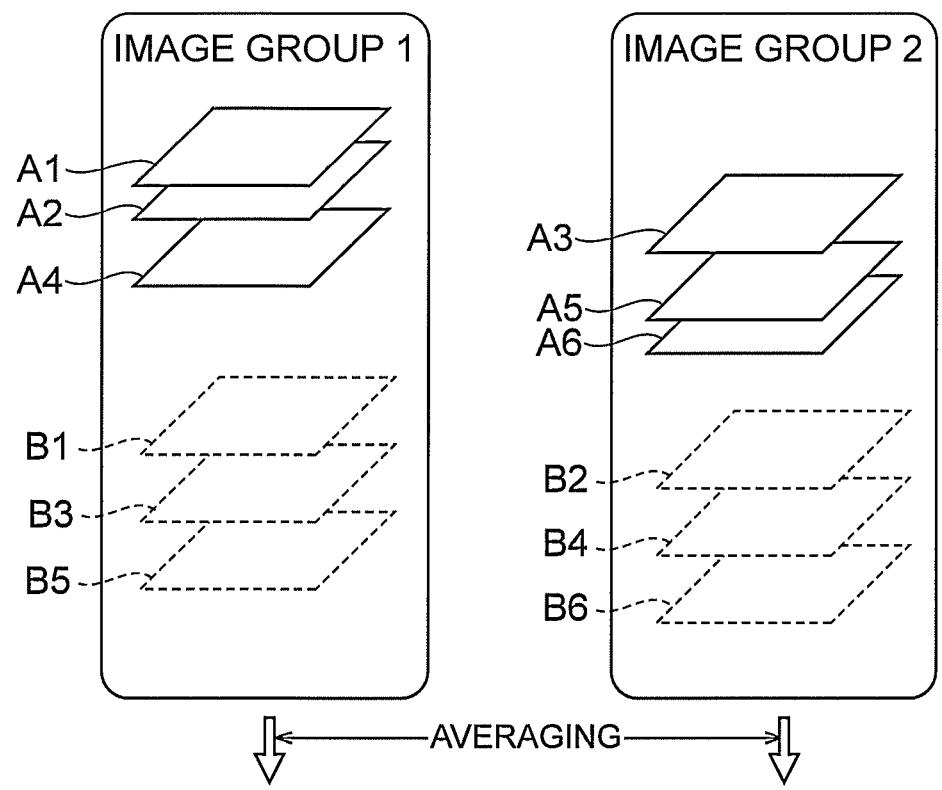
FIG. 3 includes views schematically showing a failure analysis method to be executed in the semiconductor failure analysis apparatus shown in FIG. 1.

Classification into N image groups of analysis images and background images and generation of difference images to be carried out in the image processing unit 30 will be schematically described with reference to FIG. 2 and FIG. 3. Here, FIG. 2 and FIG. 3 are views schematically showing a failure analysis method to be executed in the semiconductor failure analysis apparatus 1A shown in FIG. 1. Here, for the sake of simplification, considered is a case where the imaging position for the semiconductor device S by the imaging device 18 changes in time series to two positions P1, P2, when acquiring a plurality of analysis images (thermal images plus pattern images) and a plurality of background images (only pattern images) in time series (voltage applying step, imaging step), under the influence of temperature drift or apparatus vibration etc., and image processing to be performed in such a case will be described (image processing step).

For a position frequency distribution obtained in terms of variation in imaging position as a result of determining the imaging positions of the respective images (imaging position calculating step), the image classifying section 33 sets a region division unit ΔP to serve as an allowable range of variation in imaging position in the individual image groups after classification, as shown in (a) in FIG. 2. Then, in accordance with the region division unit ΔP, the image classifying section divides a distribution range of the imaging positions into a plurality of regions, in this example, two regions of a first region R1 and a second region R2. At this time, in the example of (a) in FIG. 2, the imaging position P1 belongs to the region R1, and the imaging position P2 belongs to the region R2.

Accordingly, as shown in (b) and (c) in FIG. 2, images whose imaging positions are at the position P1 belonging to the region R1 are classified as the image group 1, and images whose imaging positions are at the position P2 belonging to the region R2 are classified as the image group 2 (image classifying step). In the example shown in FIG. 2, out of the analysis images A1 to A6 and background images B1 to B6 acquired in time series, the analysis images A1, A2, and A4 and the background images B1, B3, and B5 are classified as the image group 1. Moreover, the analysis images A3, A5, and A6 and the background images B2, B4, and B6 are classified as the image group 2.

When the analysis images and background images are classified into image groups, the difference image generating section 34 generates difference images for each of the image groups, as shown in FIG. 3 (difference image generating step). First, as shown in (a) and (b) in FIG. 3, an average analysis image A7 is generated by averaging the analysis images A1, A2, and A4 classified in the image group 1, and an average background image B7 is generated by averaging the background images B1, B3, and B5. Similarly, an average analysis image A8 is generated by averaging the analysis images A3, A5, and A6 classified in the image group 2, and an average background image B8 is generated by averaging the background images B2, B4, and B6.

Moreover, as shown in (c) in FIG. 3, for the image group 1, a first difference image C7 (=A7−B7) is generated by taking a difference between the analysis image A7 and the background image B7. Similarly, for the image group 2, a second difference image C8 (=A8−B8) is generated by taking a difference between the analysis image A8 and the background image B8. These image group-based difference images C7 and C8 or a difference image obtained by performing processing, such as addition, averaging, selection, for the difference images C7 and C8 serves as a thermal analysis image substantially including only a thermal image and to be used for a failure analysis.

The processing corresponding to a failure analysis method to be executed in the image processing unit 30 of the failure analysis apparatus 1A shown in FIG. 1 can be realized by a semiconductor failure analysis program for causing a computer to execute image processing necessary for a failure analysis of the semiconductor device S for an image acquired by the imaging device 18. For example, the image processing unit 30 can be configured by a CPU that causes software programs necessary for the image processing to operate, a ROM in which the above-mentioned software programs and the like are stored, and a RAM in which data is temporarily stored during execution of a program. By executing a predetermined failure analysis program by the CPU in such a configuration, the image processing unit 30 and the failure analysis apparatus 1A described above can be realized.

Moreover, the above-described programs for causing image processing of a failure analysis to be executed by a CPU can be distributed in a manner recorded on a computer readable recording medium. Examples of such a recording medium include magnetic media such as hard disks and flexible disks, optical media such as CD-ROMs and DVD-ROMs, magneto-optical media such as floptical disks, and hardware devices such as, for example, RAMs, ROMs, and semiconductor nonvolatile memories specially disposed so as to execute or store program instructions.

Effects of the semiconductor failure analysis apparatus 1A, semiconductor failure analysis method, and semiconductor failure analysis program according to the present embodiment will be described.

In the semiconductor failure analysis apparatus 1A, failure analysis method, and failure analysis program shown in FIG. 1 to FIG. 3, an analysis image including a thermal image plus a pattern image in a state where a bias voltage is applied to the semiconductor device S by the voltage applying unit 14 and a background image including only a pattern image in a state where a bias voltage is not applied are acquired in plural numbers in time series, respectively. Then, for each of the analysis images and background images, an imaging position is calculated in the imaging position calculating section 32, and in the image classifying section 33, a region division unit is prepared for variation in imaging position, the analysis images and background images are classified into N image groups by means of the N regions divided by the region division unit, and generation of difference images for which thermal images are extracted is performed.

In the above-described configuration, as shown in FIG. 2 and FIG. 3, the plurality of analysis images and the plurality of background images are classified into the N image groups according to the position shift amount of a shift in imaging position, and difference images are generated for each of the image groups after classification. According to such a configuration, by appropriately setting a region division unit in the image classifying section 33, the effect of a shift in imaging position due to temperature drift, apparatus vibration, or the like can be reduced to suppress generation of noise such as an edge noise component due to a shift in imaging position in a difference image to be used for a failure analysis of the semiconductor device S.

Figure 4:
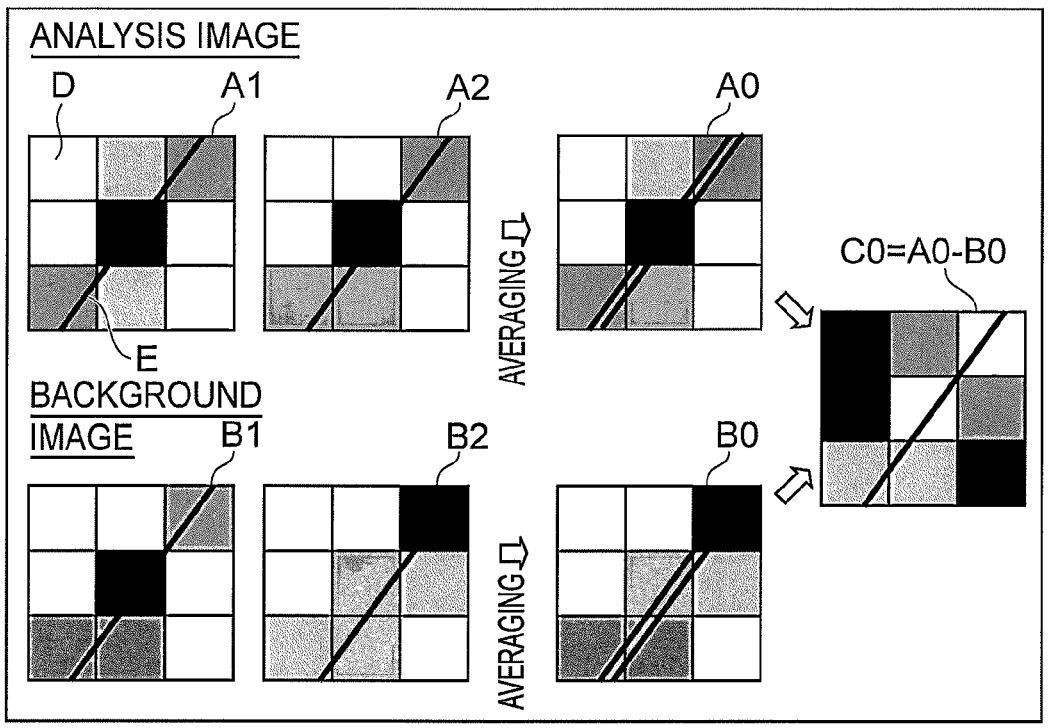
FIG. 4 includes views showing methods for generating difference images between analysis images and background images.
Figure 4:
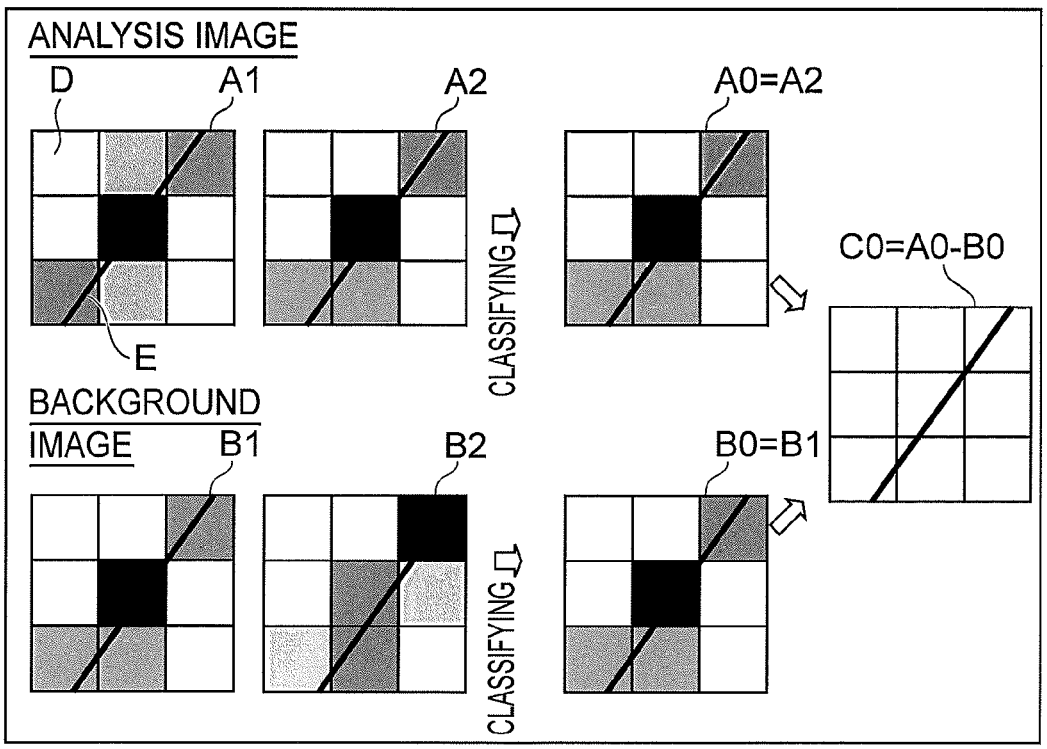

An edge noise component to be generated in a difference image between an analysis image and a background image and suppression thereof will be described with reference to FIG. 4. (a) in FIG. 4 shows a method for generating a difference image by a conventional failure analysis method. Meanwhile, (b) in FIG. 4 shows a method for generating a difference image by a failure analysis method of the above-described embodiment. In FIG. 4, each rectangular pattern denoted by reference symbol D shows one pixel (pixel size) in a two-dimensional image acquired by the imaging device 18, and each straight line denoted by reference symbol E shows an edge portion in a circuit pattern in the semiconductor device S.

In the example shown in (a) in FIG. 4, images A1 and A2 are acquired as analysis images when a bias voltage is applied, and images B1 and B2 are acquired as background images when a bias voltage is not applied. In these images, an image of the pattern edge E is acquired as a contrasting density pattern at a resolution determined by the pixel size of the pixel D. Moreover, between the analysis images A1 and A2 and between the background images B1 and B2, there is a variation in the position of the pattern edge E with respect to the pixel structure due to a shift in imaging position, and accordingly, the contrasting density patterns of pixels obtained in the respective images are different.

For such image data, an analysis image A0 is obtained as an average of the images A1 and A2, a background image B0 is obtained as an average of the images B1 and B2, and a subtraction processing of A0−B0 is performed for those images to generate a difference image C0. At this time, although no heat generation portion is included in the analysis image A0, a noise-like image due to the pattern edge E is generated under the effect of a shift in imaging position between the analysis image A0 and the background image B0. As such an edge noise component, as can be understood from (a) in FIG. 4, even if the imaging position shift is smaller than the pixel size, noise is generated as a result of shifting in the contrast pattern of pixels.

In contrast, in the example shown in (b) in FIG. 4, after performing classification of the analysis images A1 and A2 and the background images B1 and B2 into image groups according to the imaging position, a difference image is then generated. For example, in (b) in FIG. 4, the analysis image A2 and the background image B1 are almost the same in imaging position, and classified as an identical image group in image grouping. Therefore, by setting these images A2 and B1 as an analysis image A0=A2 and a background image B0=B1 in that image group, and performing a subtraction processing of A0−B0 for those images, a difference image C0 from which noise due to the pattern edge E has been removed can be obtained. Moreover, in terms also of the analysis image A1 and the background image B2, similar image processing is performed in other image groups.

Here, in the example shown in FIG. 2 and FIG. 3, it is assumed that the imaging position varies discretely between the two positions of P1 and P2 as mentioned above, but in actuality, the imaging position varies with a continuous position frequency distribution. Specifically, shifts in imaging position due to apparatus vibration occur in a normally distributed manner if a sufficient number of images have been obtained. Moreover, the standard deviation σ of the shifts in imaging position due to vibration is, normally, for example, at a level of 1/10 or less the pixel size of the imaging device 18.

Moreover, a shift in imaging position due to temperature drift is generally large when the power supply of the voltage applying unit 14 is ON, and small when the power supply is OFF. Therefore, an analysis image that is acquired in a voltage applied state and a background image that is acquired in a voltage non-applied state do not match in position shift amount, which results in a difference in the center position of a normally distributed position frequency distribution therebetween.

Figure 5:
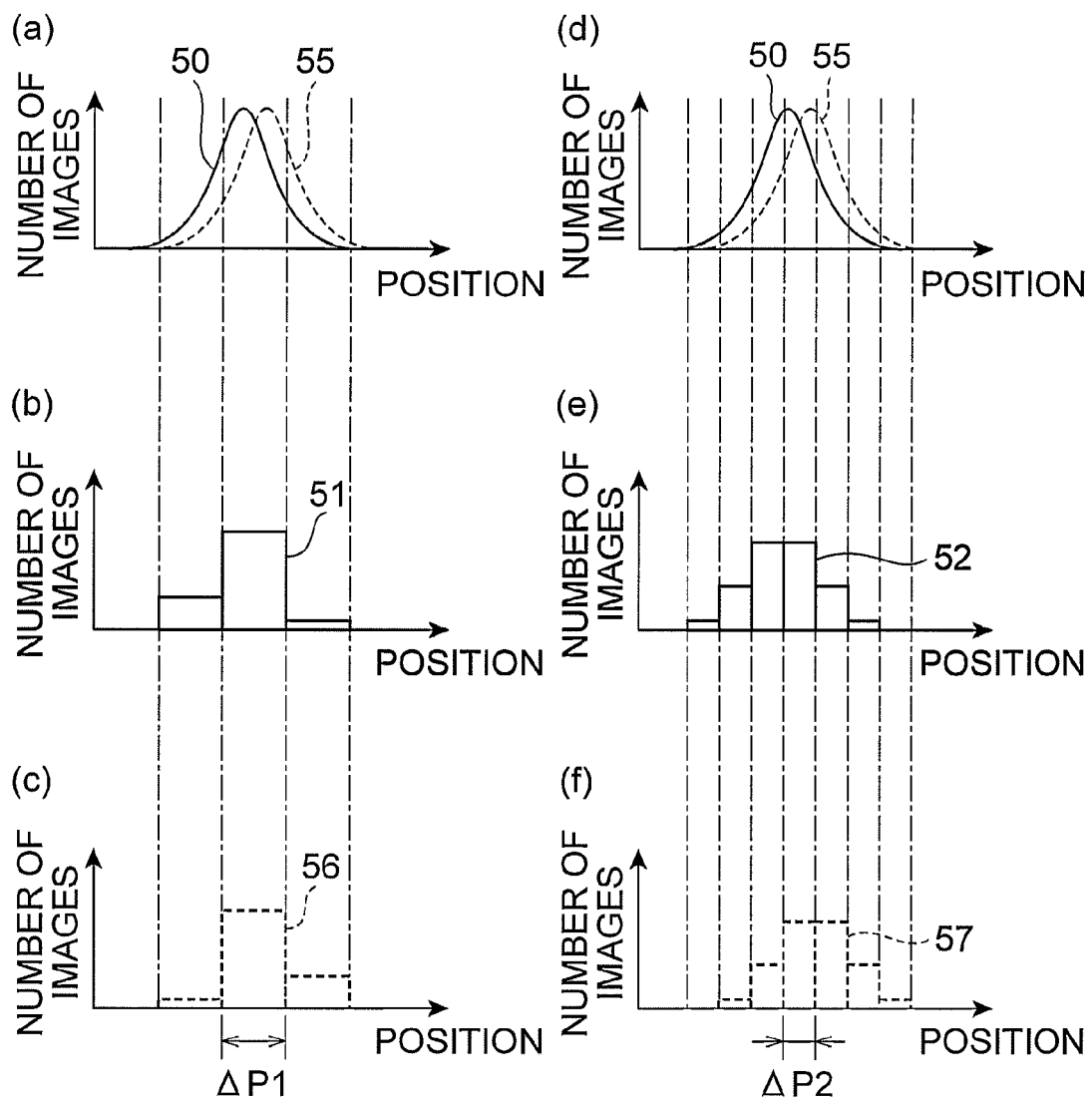
FIG. 5 includes views showing position frequency distributions of imaging positions and region division units.

FIG. 5 includes views showing position frequency distributions of imaging positions and region division units. In FIG. 5, (a), (b), and (c) in FIG. 5 show an example of classification into image groups of analysis images and background images when the region division unit is set to a larger division unit ΔP1. Meanwhile, (d), (e), and (f) in FIG. 5 show an example of classification into image groups of analysis images and background images when the region division unit is set to a smaller division unit ΔP2. Moreover, in these figures, (a) and (d) in FIG. 5 show a position frequency distribution (image number distribution) 50 of the imaging positions of analysis images and a position frequency distribution 55 of the imaging positions of background images before classification. These position frequency distributions 50 and 55 are normally distributed frequency distributions with their centers shifted.

In contrast, (b) in FIG. 5 shows a position frequency distribution (image group-based image number distribution) 51 of analysis images after classification by the division unit ΔP1, and (c) in FIG. 5 shows a position frequency distribution 56 of background images after similar classification. Meanwhile, (e) in FIG. 5 shows a position frequency distribution 52 of analysis images after classification by the division unit ΔP2, and (f) in FIG. 5 shows a position frequency distribution 57 of background images after similar classification. In setting of the region division unit ΔP, as to be described later, it is preferable to appropriately set the same in consideration of a statistical averaging effect according to the numbers of images in the respective image groups and position reproducibility in region division etc.

In terms of generation of difference images between analysis images and background images to be performed, for the classified N image groups, for each of the image groups, according to a specific method etc., for a failure analysis, there may be a configuration for generating a difference image individually for each of the N image groups, and acquiring N difference images in total. Alternatively, there may be a configuration for generating a difference image for at least one image group that is required for a failure analysis out of the N image groups.

Moreover, in terms of generation of a difference image to be finally used for a failure analysis of the semiconductor device S, for example, a configuration for performing, for the N difference images obtained respectively for the N image groups, weighting based on the numbers of images belonging to the respective image groups to thereby generate a difference image to be used for a failure analysis can be used. Moreover, specific examples of a weighting method that can be used in this case include a method of weighting and adding respective difference images and a method of weighting and averaging respective difference images.

Alternatively, for generation of a difference image, a configuration for selecting, from the N difference images obtained respectively for the N image groups, based on the numbers of images belonging to the respective image groups, a difference image to be used for a failure analysis can be used. Specific examples of a selection method that can be used in this case include a method of selecting a difference image in an image group with the largest number of images out of the N image groups. Alternatively, a method of selecting difference images in two or more image groups with large numbers of images, and calculating a final difference image by addition, averaging, etc., from those difference images may be used. According to these configurations for performing weighting for difference images, selection of an image/images, and the like, a difference image to be finally used for a failure analysis of the semiconductor device S can be suitably derived.

Moreover, in generation of a difference image to be performed in the difference image generating section 34, a configuration for making it switchable between two or more analysis modes may be used. As such a configuration, for example, a configuration for making it switchable between a first analysis mode of performing, for the N difference images respectively for the N image groups, weighting based on the numbers of images belonging to the respective image groups to thereby generate a difference image to be used for a failure analysis and a second analysis mode of selecting, based on the numbers of images belonging to the respective image groups, a difference image to be used for a failure analysis can be mentioned.

As described above, also by the configuration for allowing switching the analysis mode in the difference image generating section 34, a difference image for which a thermal image is extracted, which is actually used for a failure analysis of the semiconductor device S, can be suitably derived by selecting an analysis mode automatically or manually by an operator. In this case, specifically, it is preferable to provide a configuration for displaying an analysis mode selection screen on the display device 37, and an operator selecting an analysis mode via the input device 36 with reference to the display content. Alternatively, there may be a configuration for the difference image generating section 34 automatically setting or switching analysis modes with reference to a position frequency distribution etc., of actual images.

In the failure analysis apparatus 1A shown in FIG. 1, as the imaging device 18 for acquiring an image of the semiconductor device S, specifically, for example, an infrared InSb camera with a number of pixels of 320×240, an imaging size of 9.6 mm×7.2 mm, and a frame rate of 140 Hz having sensitivity in an infrared light wavelength range (for example, a wavelength of 3.7 µm~5.2 µm) can be used. Moreover, in a configuration having using such an infrared camera, when a 0.8× objective lens is used in the optical system 16, the overall visual field size is, by rough, X=11923 µm, Y=8931 µm, and the per-pixel size is 37 µm. Moreover, when a 4× objective lens is used, the visual field size is X=2379 µm, Y=1788 µm, and the pixel size is 7.4 µm. Moreover, when a 15× objective lens is used, the visual field size is X=629 µm, Y=474 µm, and the pixel size is 2 µm.

Moreover, it suffices to set the numbers of acquired images of analysis images (ON images) in a voltage applied state and background images (OFF images) in a voltage non-applied state according to necessity, but because image acquisition is normally performed for 1 second or more, when the imaging device with a frame rate of 140 Hz described above is used, for example, the respective numbers of images are 140 or more.

In terms of the number of images, because the larger the number of images, the closer the position frequency distribution to a normal distribution, a certain level of the number of images is necessary. In consideration of this point, it is considered to be suitable, for example, to set the image acquisition time to approximately 4 seconds to 8 seconds (number of images of 560 to 1120) for each set of the analysis images and background images. On the other hand, if the image acquisition time is long because of a large number of images, there is a possibility of a large shift in imaging position due to temperature drift. In consideration of this point, it is considered to be suitable to set the image acquisition time to 10 seconds or less for each set of the analysis images and background images.

In this case, as an example of the setting of the image acquisition time, a setting to approximately 8 seconds described above when there is weak heat generation in the semiconductor device S, to approximately 4 seconds when there is intensive heat generation, and to approximately 1 second when there is a possibility of overflow because of particularly intensive heat generation can be considered. Moreover, in terms of the number of repetitions (the number of ON/OFF times) of operations to acquire analysis images and background images, normally, an image acquisition operation for acquiring a plurality of analysis images in a predetermined time in a voltage applied state, and subsequently acquiring a plurality of background images in a predetermined time in a voltage non-applied state is performed one time, but there may be provided a configuration, in consideration of the intensity of heat generation, the number of acquired images, etc., for performing the image acquisition operation two times or more repeatedly, if necessary.

Moreover, in the failure analysis apparatus 1A having such a configuration, temperature drift that leads to variation in imaging position is caused by, for example, distortion due to expansion/contraction of metal, an asymmetric mechanism in the apparatus, imbalance in the center of gravity, and the like. Moreover, apparatus vibration is caused by, for example, a cooling mechanism such as a stirling cycle cooler of an infrared camera, resonance due to outside vibration, a microscope optical system, an optical system stage, a sample stage, and the like.

Figure 6:
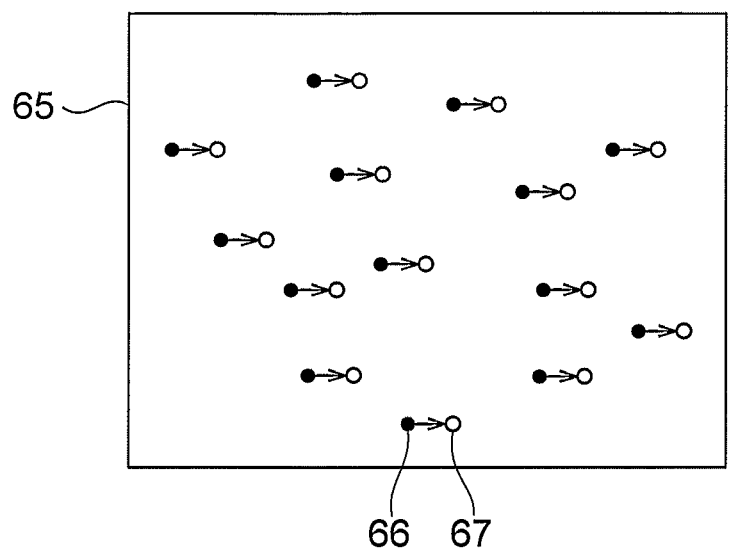
FIG. 6 includes views showing a method for deriving a position frequency distribution due to variations in imaging position.
Figure 6:
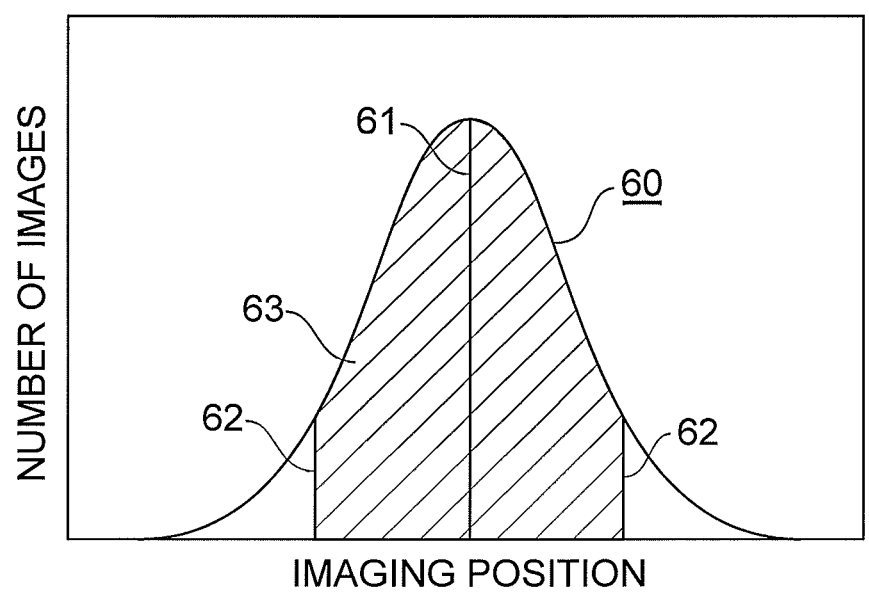

The image processing to be performed in the image processing unit 30 of the failure analysis apparatus 1A will be described more specifically. First, description will be given of calculation of the imaging positions of respective images by the imaging position calculating section 32. FIG. 6 includes views showing a method for deriving a position frequency distribution due to variations in imaging position for images of the semiconductor device S to be acquired by the imaging device 18. The calculation of the imaging positions of the respective images of analysis images and background images can be performed by using a normal image recognition technique. Specific examples of a calculation method include a method of using an average value of results of recognition by optical flow, a phase correlation method, and a method by template matching.

An example of the method for calculating the imaging position by means of optical flow will be described. While optical flow itself includes various approaches, for example, an approach by the Lucas-Kanade algorithm can be used. First, as schematically shown in the image 65 of (a) in FIG. 6, feature points (corners) 66 of a first image are recognized by the Harris operator. In terms of the number of points of the feature points 66, for example, 200 feature points are extracted from the image of a resolution of 320×240 acquired by the imaging device 18. Moreover, the extracted feature points are subpixelated.

Next, similarly, feature points 67 of a second image are recognized by the Harris operator, and the extracted feature points are subpixelated. Then, as shown by the arrows in (a) in FIG. 6, the distances between the feature points 66 and 67 (position shift amounts between the images) are measured between the first and second images. Here, the distance between the feature points is determined at each of the 200 feature points, but distance data to be obtained is less than 200 points if there are non-corresponding points.

Then, by determining an average value of the distance data between the feature points, the imaging position of the second image when the imaging position of the first image is provided as a reference position of zero is calculated. By performing such processing for each set of the pluralities of analysis images and background images, the imaging positions of the respective images and a position frequency distribution 60 thereof are obtained as shown in the graph of (b) in FIG. 6. Also, in terms of the algorithm for detecting corners to serve as feature points, specifically, other methods such as, for example, Moravec and SUSAN may be used besides Harris described above.

The position frequency distribution 60 shown in (b) in FIG. 6 is, as in FIG. 5, a frequency distribution that is normally distributed with respect to a center position 61. In terms of setting of a region division unit for such a position frequency distribution and grouping of images thereby, it is preferable, in the image classifying section 33, to obtain a position frequency distribution of the imaging positions in each set of the analysis images and background images and set a region division unit ΔP based on an average position μ1 and a distribution width w1 in the position frequency distribution of analysis images and an average position μ2 and a distribution width w2 in the position frequency distribution of background images. According to such a configuration, a region division unit can be appropriately set according to an actual state of occurrence of shifts in imaging position to classify the analysis images and background images suitably into N image groups. Also, in terms of the distribution width w of a position frequency distribution, a value such as a standard deviation σ or a half width can be used.

The setting of the region division unit ΔP for image classification will be specifically described. In the setting of a region division unit, (1) for an improvement in S/N ratio by an averaging effect, the numbers of images in the respective image groups are preferably large, and it is therefore necessary to set the division unit ΔP wide. On the other hand, (2) in consideration of an improvement in the effect of removing an edge noise component, the position reproducibility in region division is preferably high, and it is therefore necessary to set the division unit ΔP narrow. Therefore, it is preferable to set the region division unit ΔP in consideration of the balance between the conditions (1) and (2).

Moreover, in such a case, for example, as determining a difference image to be finally used for a failure analysis by performing weighting based on the numbers of images in the respective image groups, in the normally distributed position frequency distribution 60 shown in (b) in FIG. 6, an image group including the center average position 61 has the greatest effect on a final difference image. In consideration of such a point, it is considered to be of primary importance to appropriately set a divisional range for the image group including the average position 61.

Based on normal distribution characteristics, if the standard deviation σ is provided as the distribution width w of the position frequency distribution 60, the probability that the imaging position is included in a range with a position shift from the average position μ (position 61 in (b) in FIG. 6) of ±1σ is 68.3%, the probability to be included in a range of ±1.5σ is 86.6%, and the probability to be included in a range of ±2σ is 95.4%. In actuality, the number of images to be acquired is limited, and moreover, a recognition gap in imaging position due to noise, a lack of recognition accuracy, etc., also occurs. For this reason, if the position range of the region division unit ΔP is set wide to approximately ±2σ, the frequency that an image is obtained is reduced at a position separated ±2σ from an average position μ, and also possibly becomes a noise component. Specifically, where the frequency at the average position μ is provided as 100%, the frequency at a position μ±2σ is 13.5%.

In consideration of these normal distribution characteristics etc., here, a position range of μ±1.5σ is adopted as a standard region division unit ΔP. In (b) in FIG. 6, left and right imaging positions 62 show positions separated ±1.5σ from the average position 61. In this case, where the frequency at the average position 61 (=μ) is similarly provided as 100%, the frequency at the position 62 (=μ±1.5σ) is 32.5%. Moreover, in (b) in FIG. 6, the number of images to be included in a range 63 with a position shift from the average position μ of within ±1.5σ is 86.6% with respect to the whole number of images.

Figure 7:
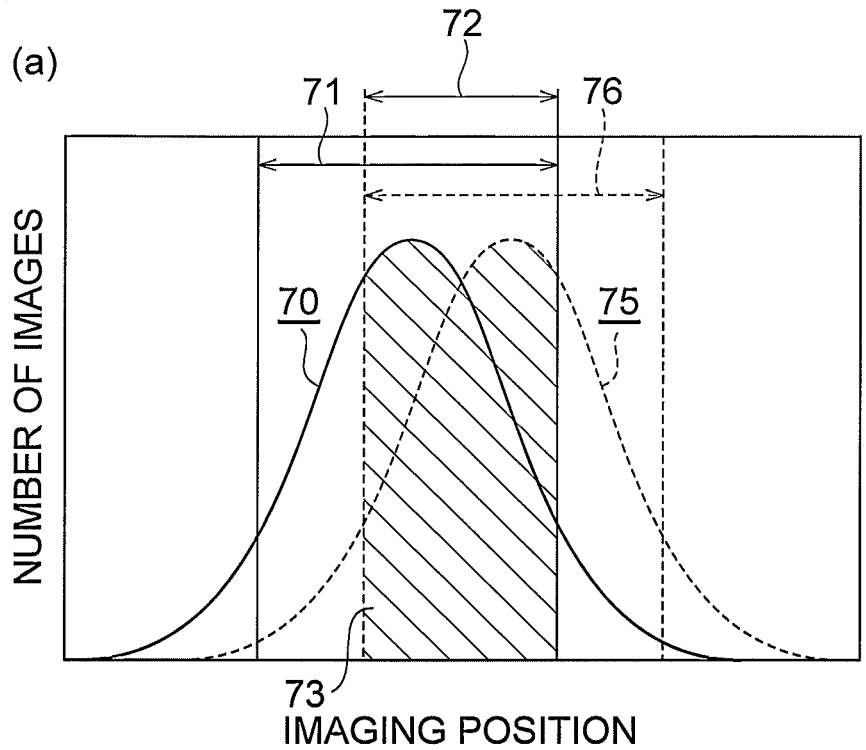
FIG. 7 includes views showing a method for setting a region division unit with reference to position frequency distributions.
Figure 7:
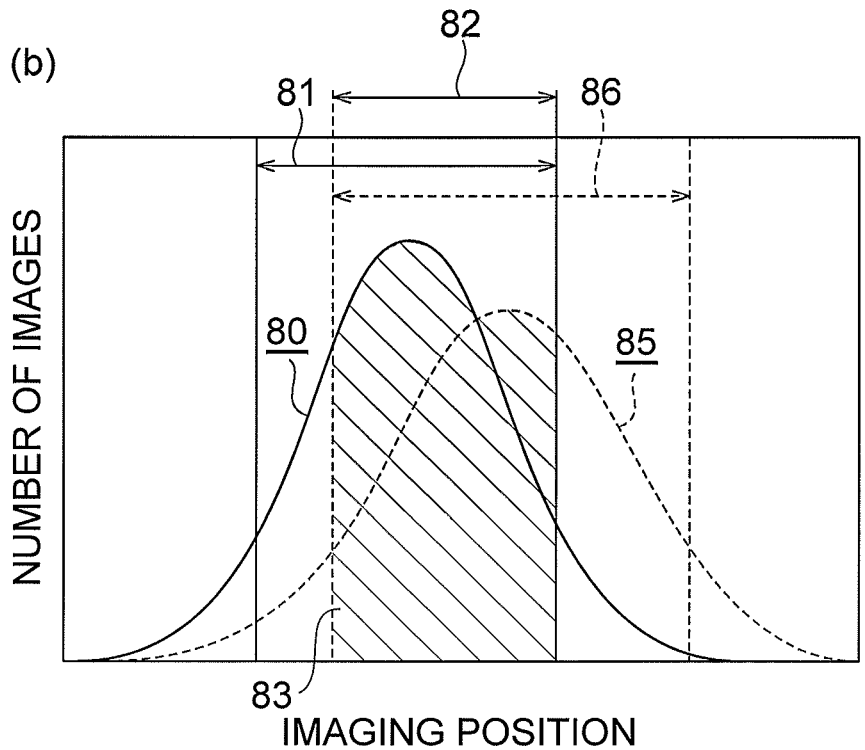

FIG. 7 includes views showing a setting method when setting a region division unit with reference to position frequency distributions for each set of the analysis images and background images. Here, as mentioned above regarding FIG. 5, the position frequency distributions of analysis images and background images are, normally, normally distributed frequency distributions with their centers shifted from each other. In this case, in setting of the region division unit ΔP, it is preferable to take both of the two position frequency distributions thereof into consideration. As such a setting method, specifically, a method of determining a region unit for analysis images and a region unit for background images, and setting a common range of those region units (a range where the region units are overlapped, a product set of the region units) as the region division unit ΔP can be used.

In the example shown in (a) in FIG. 7, in a position frequency distribution 70 of analysis images and a position frequency distribution of background images, the standard deviations σ1 and σ2 corresponding to their distribution widths w1 and w2 have the same value σ. Moreover, their average positions μ1 and μ2 are different positions with a position shift amount=σ.

Moreover, in the graph of (a) in FIG. 7, a region unit 71 for analysis images indicates a range of ±1.5σ from the average position μ1 of the position frequency distribution 70. Similarly, a region unit 76 for background images indicates a range of ±1.5σ from the average position μ2 of the position frequency distribution 75. For these region units 71 and 76, the region division unit ΔP is set by a common range 72 thereof. Moreover, at this time, the number of images to be included in a range 73 to be a center region of regions divided by the region division unit ΔP is 52.4% with respect to the whole number of images.

In the example shown in (b) in FIG. 7, in a position frequency distribution 80 of analysis images and a position frequency distribution 85 of background images, the standard deviations σ1 and σ2 corresponding to their distribution widths w1 and w2 are different, and σ2=1.2×σ1. Moreover, their average positions μ1 and μ2 are different positions with a position shift amount=σ1.

Moreover, in the graph of (b) in FIG. 7, a region unit 81 for analysis images indicates a range of ±1.5σ1 from the average position μ1 of the position frequency distribution 80. Similarly, a region unit 86 for background images indicates a range of ±1.5σ2 from the average position μ2 of the position frequency distribution 85. For these region units 81 and 86, the region division unit ΔP is set by a common range 82 thereof. Moreover, at this time, the number of images to be included in a range 83 to be a center region of regions divided by the region division unit ΔP is 56.9% with respect to the whole number of images.

Moreover, in the setting example of a region division unit described above, the position range of μ±1.5σ is set as a standard region division unit ΔP, but in terms of the factor of 1.5 to determine a division unit for the standard deviation σ (generally, the distribution width w) may be provided as an adjustment factor α that can be changed automatically or manually by an operator. In this case, specifically, a configuration for, in the image classifying section 33, setting the adjustment factor α to adjust the region division unit ΔP, determining a region unit μ1±α×w1 for analysis images and a region unit μ2±α×w2 for background images, and setting a common range of those region units as the region division unit ΔP can be used. Moreover, for the method for setting the region division unit ΔP, various configurations may be used, without limitation to such a configuration.

Further, in terms of a specific value setting of the adjustment factor α, it is preferable to determine the distribution width w1 in the position frequency distribution of analysis images and the distribution width w2 in the position frequency distribution of background images by the standard deviations σ1 and σ2, and set the adjustment factor α variable within a range satisfying a condition of 1≤α≤2 with α=1.5 described above provided as a center value. By setting the numerical range of the adjustment factor α with respect to the standard deviations σ1 and σ2 as in the above, the region division unit ΔP can be appropriately set for a position frequency distribution due to variations in imaging position. Moreover, in setting and changing of the adjustment factor α, it is preferable to consider the balance between the condition (1) for improving the S/N ratio and the condition (2) for improving the effect of removing an edge noise component mentioned above.

Moreover, in the configuration for using the adjustment factor α in the setting of the region division unit ΔP, a configuration for automatically setting the adjustment factor α in the image classifying section 33 according to a specific failure analysis condition etc., can be used. Alternatively, a configuration for manually setting the adjustment factor α based on a factor value input via the input device 36 by an operator may be used. In such a configuration for manual setting, the region division unit ΔP can be suitably set based on an operator's decision in consideration of an actual state of occurrence of shifts in imaging position and a specific analysis condition etc., of the semiconductor device.

Figure 8:
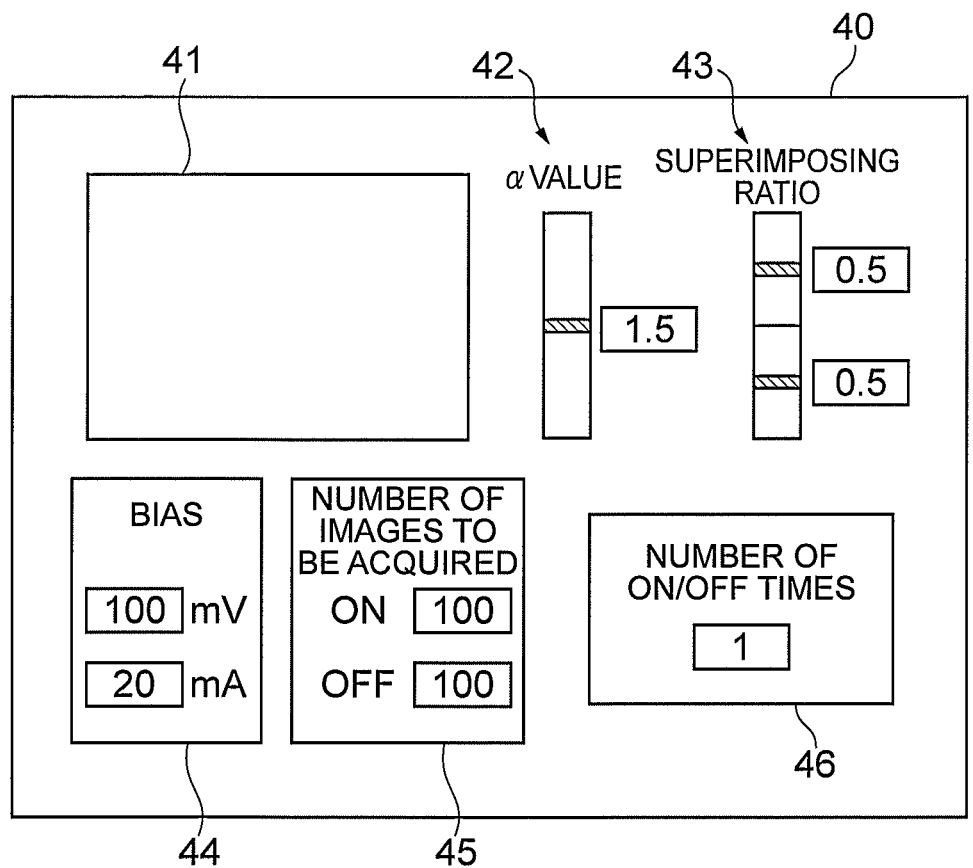
FIG. 8 is a view showing an example of an operation screen displayed on a display device.

FIG. 8 is a view showing an example of an operation screen displayed on the display device 37 regarding the setting of the adjustment factor α. In the operation screen 40, there is provided an image display region 41, an α-value setting region 42, and a superimposing ratio setting region 43 at an upper part thereof. The image display region 41 is used when displaying an image such as an analysis image, a background image, or a difference image acquired for the semiconductor device S. Moreover, in the image display region 41, there may be a configuration for displaying a normal pattern image of the semiconductor device S or a layout image including design information of the semiconductor device S etc., in addition to a thermal analysis image acquired in the present apparatus 1A, if necessary.

The α-value setting region 42 is used for manual setting and changing of the adjustment factor α to be used when setting the region division unit ΔP. In the example shown in FIG. 8, the setting region 42 is provided with a setting knob for setting the value of the adjustment factor α in the range of 1.0≤α≤2.0 with 1.5 provided as a standard value. Moreover, the superimposing ratio setting region 43 is used for setting and changing of superimposing ratios to be used when displaying, in the image display region 41, a normal pattern image and a layout image superimposed on a thermal analysis image. In the example shown in FIG. 8, the setting region 43 is provided with two setting knobs for setting the superimposing ratios of a pattern image and a layout image. Moreover, in the setting regions 42 and 43, there is a configuration for allowing also manual input of setting numerical values, respectively.

Also, at a lower part of the operation screen 40, there is further provided a bias setting region 44, a number-of-images-to-be-acquired setting region 45, and a number-of-ON/OFF-times setting region 46. The bias setting region 44 is used when setting the values of a bias voltage and bias current to be supplied from the power supply of the voltage applying unit 14 to the semiconductor device S. Moreover, the number-of-images-to-be-acquired setting region 45 is used when setting the number of analysis images to be acquired in a voltage applied state (power supply ON) and the number of background images to be acquired in a voltage non-applied state (power supply OFF). Moreover, the number-of-ON/OFF-times setting region 46 is used when setting how many times to perform an image acquisition operation by acquisition of a plurality of analysis images in a power-ON state and acquisition of a plurality of background images in a power-OFF state.

Figure 9:
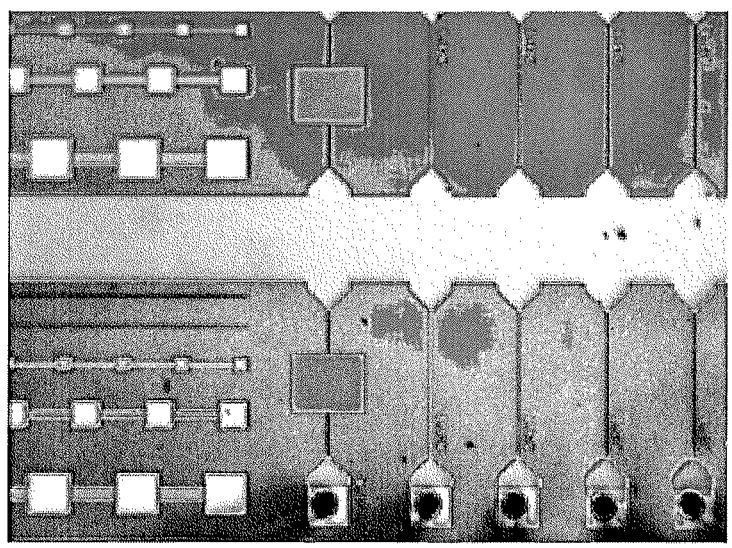
FIG. 9 is a view showing a normal pattern image of a semiconductor device.

A thermal analysis image to be acquired by means of the semiconductor failure analysis apparatus 1A and failure analysis method according to the above-described embodiment will be described along with its specific examples. FIG. 9 is a view showing a normal pattern image of the semiconductor device S to serve as an analysis object. Such a pattern image is acquired by means of, for example, the imaging device 18 or an imaging system provided separately from the imaging device 18. Here, the semiconductor device S having such a circuit pattern is biased with a voltage of 100 mV and a current of 20 mA by the voltage applying unit 14, and a thermal image thereof is acquired.

Figure 10:
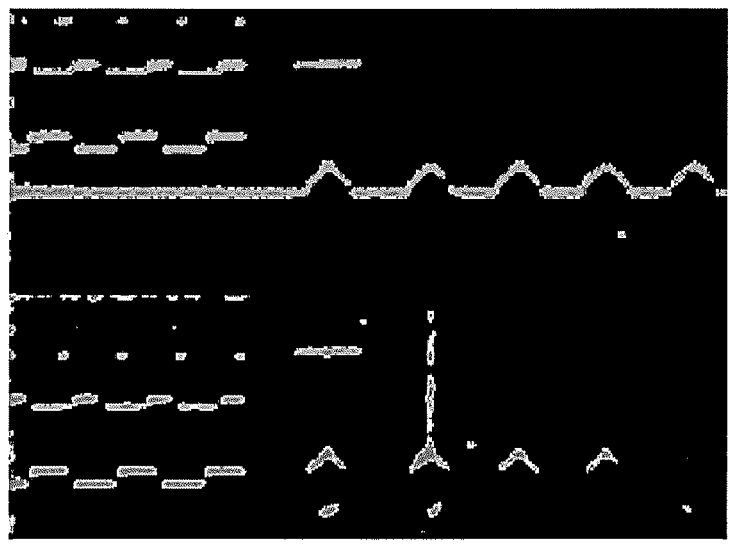
FIG. 10 includes views showing examples of difference images between analysis images and background images.
Figure 10:
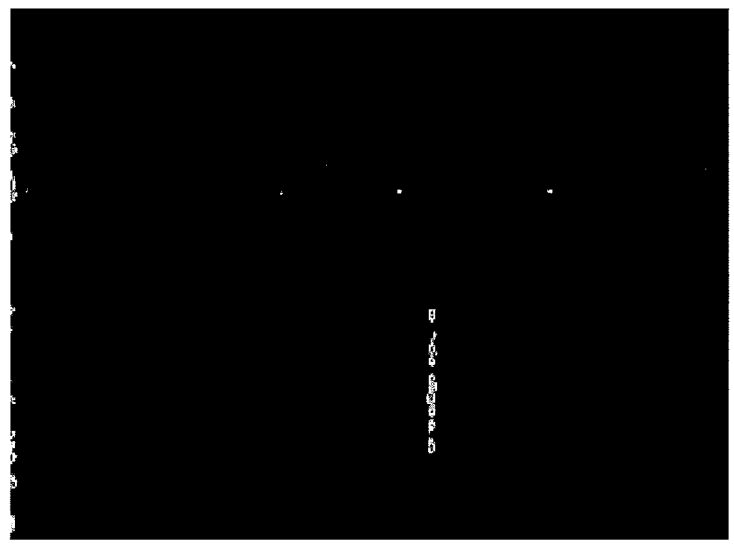
Figure 11:
FIG. 11 includes views showing examples of difference images between analysis images and background images.
Figure 11:
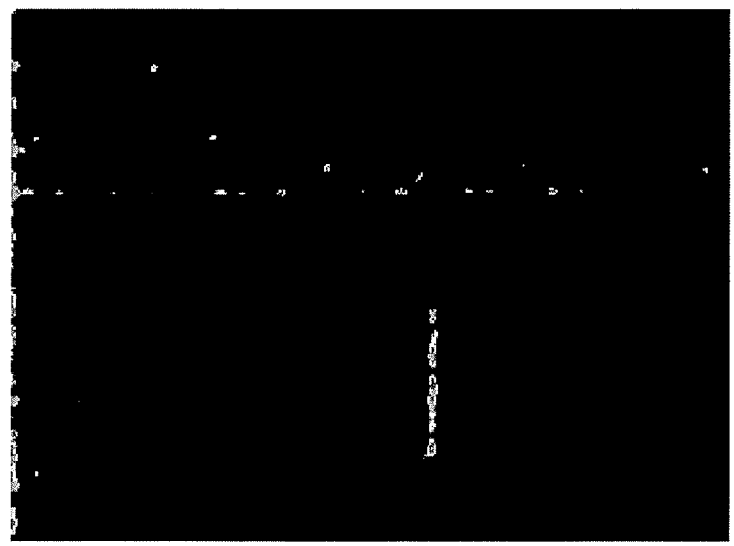
Figure 12:
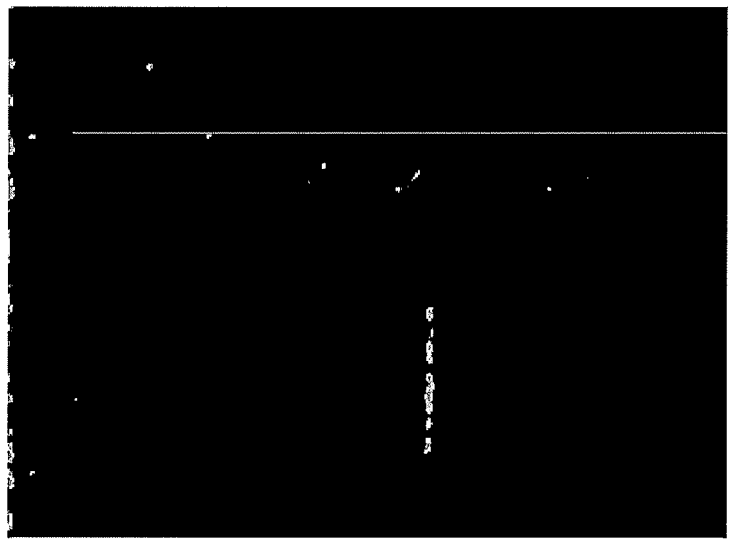
FIG. 12 includes views showing examples of difference images between analysis images and background images.
Figure 12:
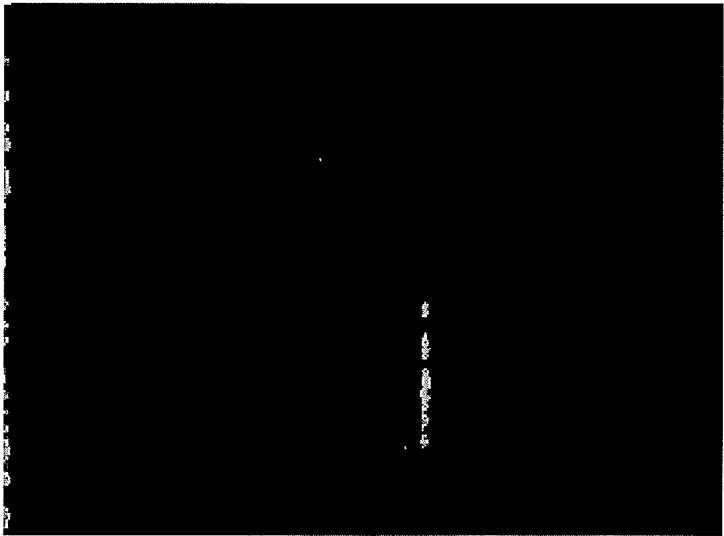

FIG. 10 to FIG. 12 include views showing examples of difference images (thermal analysis images) between analysis images and background images, respectively. In addition, all images shown in FIG. 10 to FIG. 12 below are images applied with smoothing.

(a) in FIG. 10 shows a difference image generated by a conventional method where classification of analysis images and background images according to the imaging position is not performed. When the difference image is compared with the pattern image shown in FIG. 9, it can be understood that, in the difference image by the conventional method, an edge noise component due to a pattern edge of the semiconductor device S has been generated under the influence of a shift in imaging position between analysis images and background images.

Moreover, the average position μ1 and the standard deviation σ1 for the analysis images, and the average position μ2 and the standard deviation σ2 for the background images were determined at this time in terms of the X-axis direction and Y-axis direction, respectively, as follows.

Average position: μ1X=0.025, μ1Y=0.010
Standard deviation: σ1X=0.040, σ1Y=0.029
Average position: μ2X=0.026, μ2Y=0.021
Standard deviation: σ2X=0.025, σ2Y=0.018

Here, the numerical values of the average positions and standard deviations described above are pixel shift amounts when images were acquired by using a 4× objective lens as the objective lens in the light guide optical system 16. For example, the pixel shift amount in the Y-axis direction between the analysis images and background images is $\mu2Y-\mu1Y=0.011$ pixels, which corresponds to approximately 0.08 $\mu$m in terms of the position shift amount.

(b) in FIG. 10 shows a difference image generated by the method of the above-described embodiment where analysis images and background images are classified according to the imaging position. The difference image was obtained under a condition of the adjustment factor provided as $\alpha=1$, the region division unit $\Delta P$ set by $1\sigma$, and the division number of regions provided as N=9 in the specific method mentioned above. It can be understood that, in the difference image thus obtained by using the method for classifying analysis images and background images into image groups, the effect of a shift in imaging position is reduced, an edge noise component that had been generated in a difference image by the conventional method is removed, and a thermal image to be used for a failure analysis of the semiconductor device S can be clearly confirmed.

Moreover, such an effect of removing an edge noise component changes as a result of changing the region division unit $\Delta P$. (a) in FIG. 11 shows a difference image obtained under a condition of the adjustment factor provided as $\sigma=1.5$ and the division number of regions provided as N=5. Meanwhile, (b) in FIG. 11 shows a difference image obtained under a condition of the adjustment factor provided as $\alpha=2$ and the division number of regions provided as N=5. In these difference images, when the value of the adjustment factor $\alpha$ is set larger to make the region division unit $\Delta P$ wider, the effect of removing an edge noise component is reduced. However, as mentioned above, because the S/N ratio is degraded when the region division unit $\Delta P$ is set narrow conversely, in setting of the region division unit $\Delta P$, it is preferable to consider the balance of those conditions.

Moreover, in terms of handling of the image groups into which analysis images and background images have been classified, there is provided a configuration for using all the N image groups for difference image generation, and a configuration for selecting some (one or a plurality of) image groups with large numbers of images out of the N image groups and using the same for difference image generation. Generally, the method of using all image groups is advantageous for an improvement in S/N ratio by an averaging effect. On the other hand, for an improvement in the effect of removing an edge noise component, the method of selecting and using some image groups is advantageous. Therefore, in terms of also which of these methods to use, it is necessary to consider the balance of those conditions.

When pluralities of analysis images and background images are classified into N image groups, the image group in which the average position $\mu$ is included is the largest in the number of images included in the image group, and the number of images decreases as it separates from the average position $\mu$ (refer to FIG. 5 to FIG. 7). In this case, in an image group that is at a position distant from the average position, deviation in position is likely to occur because the number of images is small, and an edge noise component is easily generated when a difference is taken. For this reason, depending on the number of obtained images, the S/N ratio, and specific imaging conditions, etc., a better result may be obtained with the configuration for selecting and using not all but some of the image groups.

(a) in FIG. 12 shows a difference image obtained by setting the adjustment factor to $\alpha=1.5$ and setting the division number of regions to N=5 and using all of the five image groups. Meanwhile, (b) in FIG. 12 shows a difference image obtained by the same setting of the adjustment factor to $\alpha=1.5$ and the division number of regions to N=5 and by using only one image group including the average position. Of these difference images, the difference image using only the image group including the average position is further improved in the effect of removing an edge noise component.

The semiconductor failure analysis apparatus, failure analysis method, and failure analysis program according to the present invention is not limited to the embodiment and configuration examples mentioned above, and various modifications can be made. For example, in terms of the configuration of the stage 10, the voltage applying unit 14, the light guide optical system 16, and the imaging device 18 etc., to be used for image acquisition of the semiconductor device S, various configurations may be specifically used besides the configuration described above.

In the semiconductor failure analysis apparatus according to the above-mentioned embodiment, used is a configuration, which is a semiconductor failure analysis apparatus for performing a failure analysis by means of a thermal image of a semiconductor device, including (1) voltage applying means for applying a bias voltage to a semiconductor device to serve as an analysis object, (2) imaging means for acquiring an image of the semiconductor device, and (3) image processing means for performing image processing necessary for a failure analysis of the semiconductor device for an image acquired by the imaging means, in which (4) the imaging means acquires a plurality of analysis images each including a thermal image in a state where the bias voltage is applied to the semiconductor device and a plurality of background images in a state where the bias voltage is not applied thereto, and (5) the image processing means includes imaging position calculating means for calculating, for each of the plurality of analysis images and the plurality of background images, an imaging position thereof, image classifying means for preparing, for the imaging position of each of the plurality of analysis images and the plurality of background images, a region division unit set with reference to a position frequency distribution of the imaging positions, and classifying the plurality of analysis images and the plurality of background images into N image groups (N is an integer not less than 2) according to which of the N regions divided in accordance with the region division unit the imaging position belongs to, and difference image generating means for generating a difference image between the analysis image and the background image to be used for a failure analysis, individually for the classified N image groups.

In the semiconductor failure analysis method according to the above-mentioned embodiment, used is a configuration, which is a semiconductor failure analysis method for performing a failure analysis by means of a thermal image of a semiconductor device, including (1) a voltage applying step of applying a bias voltage to a semiconductor device to serve as an analysis object, (2) an imaging step of acquiring an image of the semiconductor device, and (3) an image processing step of performing image processing necessary for a failure analysis of the semiconductor device for an image acquired by the imaging step, in which (4) the imaging step acquires a plurality of analysis images each including a thermal image in a state where the bias voltage is applied to the semiconductor device and a plurality of background images in a state where the bias voltage is not applied thereto, and (5) the image processing step includes an imaging position calculating step of calculating, for each of the plurality of analysis images and the plurality of background images, an imaging position thereof, an image classifying step of preparing, for the imaging position of each of the plurality of analysis images and the plurality of background images, a region division unit set with reference to a position frequency distribution of the imaging positions, and classifying the plurality of analysis images and the plurality of background images into N image groups (N is an integer not less than 2) according to which of the N regions divided in accordance with the region division unit the imaging position belongs to, and a difference image generating step of generating a difference image between the analysis image and the background image to be used for a failure analysis, individually for the classified N image groups.

Here, in terms of classification of analysis images and background images into N image groups, it is preferable to obtain the position frequency distribution of the imaging positions of each set of the plurality of analysis images and the plurality of background images, and set the region division unit to be used for classification based on an average position µ1 and a distribution width w1 in the position frequency distribution of the plurality of analysis images and an average position µ2 and a distribution width w2 in the position frequency distribution of the plurality of background images. According to such a configuration, a region division unit can be appropriately set according to an actual state of occurrence of shifts in imaging position in image acquisition of a semiconductor device to classify the plurality of analysis images and the plurality of background images suitably into N image groups.

In terms of setting of the region division unit in the above-described configuration, specifically, a configuration of setting an adjustment factor α to adjust the region division unit, determining a region unit µ1±α×w1 for the plurality of analysis images and a region unit µ2±α×w2 for the plurality of background images, and setting a common range of the region units as the region division unit can be used. Moreover, in terms of the method for setting the region division unit, without limitation to such a configuration, various configurations may be used.

Moreover, in the configuration for using the adjustment factor α in the setting of the region division unit as in the above, a configuration for automatically setting the adjustment factor α according to a specific failure analysis condition etc., can be used. Alternatively, a configuration for manually setting the adjustment factor α based on a factor value input by an operator may be used. In such a configuration for manual setting, the region division unit can be suitably set based on an operator's decision in consideration of an actual state of occurrence of shifts in imaging position and a specific analysis condition etc., of the semiconductor device.

Further, in terms of a specific setting of the adjustment factor α described above, it is preferable to determine the distribution width w1 in the position frequency distribution of the plurality of analysis images and the distribution width w2 in the position frequency distribution of the plurality of background images by standard deviations σ1 and σ2, respectively, and set the adjustment factor α within a range satisfying a condition of $1 \leq \alpha \leq 2$. By setting the numerical range of the adjustment factor α with respect to the standard deviations σ1 and σ2 as in the above, the region division unit can be appropriately set for a position frequency distribution due to variations in imaging position.

In terms of generation of difference images between analysis images and background images, a configuration for performing, for the N difference images obtained respectively for the N image groups, weighting based on the numbers of images belonging to the respective image groups to thereby generate a difference image to be used for a failure analysis can be used. Alternatively, a configuration for selecting, from the N difference images obtained respectively for the N image groups, based on the numbers of images belonging to the respective image groups, a difference image to be used for a failure analysis can be used. According to these configurations, a difference image to be finally used for a failure analysis of the semiconductor device can be suitably derived.

Moreover, in terms of generation of a difference image, there may be a configuration for being switchable between a first analysis mode of performing, for the N difference images obtained respectively for the N image groups, weighting based on the numbers of images belonging to the respective image groups to thereby generate a difference image to be used for a failure analysis, and a second analysis mode of selecting, based on the numbers of images belonging to the respective image groups, a difference image to be used for a failure analysis. Also by such a configuration, a difference image to be finally used for a failure analysis of the semiconductor device can be suitably derived by selecting an analysis mode automatically or manually by an operator.

INDUSTRIAL APPLICABILITY

The present invention can be used as a semiconductor failure analysis apparatus, failure analysis method, and failure analysis program capable of suppressing the effect of a shift in imaging position in a thermal analysis image to be used for a failure analysis of a semiconductor device.

REFERENCE SIGNS LIST

1A—semiconductor failure analysis apparatus, S—semiconductor device, 10—sample stage, 12—stage drive unit, 14—voltage applying unit, 16—light guide optical system, 18—imaging device, 20—control unit, 21—imaging control section, 22—stage control section, 23—synchronization control section, 30—image processing unit, 31—image storing section, 32—imaging position calculating section, 33—image classifying section, 34—difference image generating section, 36—input device, 37—display device.

The invention claimed is:
1. A semiconductor failure analysis apparatus for performing a failure analysis by means of a thermal image of a semiconductor device, comprising:
   voltage applying means applying a bias voltage to a semiconductor device to serve as an analysis object;
   imaging means acquiring an image of the semiconductor device; and
   image processing means performing image processing necessary for a failure analysis of the semiconductor device for an image acquired by the imaging means, wherein
   the imaging means acquires a plurality of analysis images each including a thermal image in a state where the bias voltage is applied to the semiconductor device and a plurality of background images in a state where the bias voltage is not applied thereto, and
   the image processing means includes:
   imaging position calculating means calculating, for each of the plurality of analysis images and the plurality of background images, an imaging position thereof;
   image classifying means preparing, for the imaging position of each of the plurality of analysis images and the plurality of background images, a region division unit set with reference to a position frequency distribution of the imaging positions, and classifying the plurality of analysis images and the plurality of background images into N image groups (N is an integer not less than 2)

according to which of the N regions divided in accordance with the region division unit the imaging position belongs to; and difference image generating means generating a difference image between the analysis image and the background image to be used for a failure analysis, individually for the classified N image groups.

2. The semiconductor failure analysis apparatus according to claim 1, wherein the image classifying means obtains the position frequency distribution of the imaging positions of each set of the plurality of analysis images and the plurality of background images, and sets the region division unit based on an average position $\mu1$ and a distribution width $w1$ in the position frequency distribution of the plurality of analysis images and an average position $\mu2$ and a distribution width $w2$ in the position frequency distribution of the plurality of background images.

3. The semiconductor failure analysis apparatus according to claim 2, wherein the image classifying means sets an adjustment factor $\alpha$ to adjust the region division unit, determines a region unit $\mu1\pm\alpha\times w1$ for the plurality of analysis images and a region unit $\mu2\pm\alpha\times w2$ for the plurality of background images, and sets a common range of the region units as the region division unit.

4. The semiconductor failure analysis apparatus according to claim 3, wherein the image classifying means sets the adjustment factor $\alpha$ based on a factor value input by an operator.

5. The semiconductor failure analysis apparatus according to claim 3, wherein the image classifying means determines each of the distribution width $w1$ in the position frequency distribution of the plurality of analysis images and the distribution width $w2$ in the position frequency distribution of the plurality of background images by a standard deviation $\sigma$, and sets the adjustment factor $\alpha$ within a range satisfying a condition of $1\leq\alpha\leq2$.

6. The semiconductor failure analysis apparatus according to claim 1, wherein the difference image generating means performs, for the N difference images obtained respectively for the N image groups, weighting based on the numbers of images belonging to the respective image groups to thereby generate a difference image to be used for a failure analysis.

7. The semiconductor failure analysis apparatus according to claim 1, wherein the difference image generating means selects, from the N difference images obtained respectively for the N image groups, based on the numbers of images belonging to the respective image groups, a difference image to be used for a failure analysis.

8. The semiconductor failure analysis apparatus according to claim 1, wherein the difference image generating means is configured to be switchable between a first analysis mode of performing, for the N difference images obtained respectively for the N image groups, weighting based on the numbers of images belonging to the respective image groups to thereby generate a difference image to be used for a failure analysis, and a second analysis mode of selecting, based on the numbers of images belonging to the respective image groups, a difference image to be used for a failure analysis.

9. A semiconductor failure analysis method for performing a failure analysis by means of a thermal image of a semiconductor device, comprising:

a voltage applying step of applying a bias voltage to a semiconductor device to serve as an analysis object;
an imaging step of acquiring an image of the semiconductor device; and
an image processing step of performing image processing necessary for a failure analysis of the semiconductor device for an image acquired by the imaging step, wherein the imaging step acquires a plurality of analysis images each including a thermal image in a state where the bias voltage is applied to the semiconductor device and a plurality of background images in a state where the bias voltage is not applied thereto, and the image processing step includes:
an imaging position calculating step of calculating, for each of the plurality of analysis images and the plurality of background images, an imaging position thereof;
an image classifying step of preparing, for the imaging position of each of the plurality of analysis images and the plurality of background images, a region division unit set with reference to a position frequency distribution of the imaging positions, and classifying the plurality of analysis images and the plurality of background images into N image groups (N is an integer not less than 2) according to which of the N regions divided in accordance with the region division unit the imaging position belongs to; and
a difference image generating step of generating a difference image between the analysis image and the background image to be used for a failure analysis, individually for the classified N image groups.

10. The semiconductor failure analysis method according to claim 9, wherein the image classifying step obtains the position frequency distribution of the imaging positions of each set of the plurality of analysis images and the plurality of background images, and sets the region division unit based on an average position $\mu1$ and a distribution width $w1$ in the position frequency distribution of the plurality of analysis images and an average position $\mu2$ and a distribution width $w2$ in the position frequency distribution of the plurality of background images.

11. The semiconductor failure analysis method according to claim 10, wherein the image classifying step sets an adjustment factor $\alpha$ to adjust the region division unit, determines a region unit $\mu1\pm\alpha\times w1$ for the plurality of analysis images and a region unit $\mu2\pm\alpha\times w2$ for the plurality of background images, and sets a common range of the region units as the region division unit.

12. The semiconductor failure analysis method according to claim 11, wherein the image classifying step sets the adjustment factor $\alpha$ based on a factor value input by an operator.

13. The semiconductor failure analysis method according to claim 11, wherein the image classifying step determines each of the distribution width $w1$ in the position frequency distribution of the plurality of analysis images and the distribution width $w2$ in the position frequency distribution of the plurality of background images by a standard deviation $\sigma$, and sets the adjustment factor $\alpha$ within a range satisfying a condition of $1\leq\alpha\leq2$.

14. The semiconductor failure analysis method according to claim 9, wherein the difference image generating step performs, for the N difference images obtained respectively for the N image groups, weighting based on the numbers of images belonging to the respective image groups to thereby generate a difference image to be used for a failure analysis.

15. The semiconductor failure analysis method according to claim 9, wherein the difference image generating step selects, from the N difference images obtained respectively for the N image groups, based on the numbers of images belonging to the respective image groups, a difference image to be used for a failure analysis.

16. The semiconductor failure analysis method according to claim 9, wherein the difference image generating step is configured to be switchable between a first analysis mode of performing, for the N difference images obtained respectively for the N image groups, weighting based on the numbers of images belonging to the respective image groups to thereby generate a difference image to be used for a failure analysis, and a second analysis mode of selecting, based on the numbers of images belonging to the respective image groups, a difference image to be used for a failure analysis.

\* \* \* \* \*